United States Patent [19]

Clarke et al.

[11] Patent Number: 5,225,679

[45] Date of Patent: Jul. 6, 1993

[54] METHODS AND APPARATUS FOR DETERMINING HYDROCARBON FUEL PROPERTIES

[75] Inventors: Richard H. Clarke, Scituate; Deming Tang, Brighton, both of Mass.

[73] Assignee: Boston Advanced Technologies, Inc., Newton, Mass.

[21] Appl. No.: 825,062

[22] Filed: Jan. 24, 1992

[51] Int. Cl.⁵ .................... G01N 21/35; G01N 33/22
[52] U.S. Cl. ................................ 250/343; 250/339
[58] Field of Search ............ 250/301, 339, 343, 340, 250/341

[56] References Cited

U.S. PATENT DOCUMENTS

| | | | |
|---|---|---|---|
| 2,593,391 | 4/1952 | Bray | 250/53 |
| 3,061,723 | 10/1962 | Kapff | 250/71 |
| 3,697,226 | 10/1972 | Hirschfeld et al. | 23/254 |
| 3,725,658 | 4/1973 | Stanley et al. | 250/71 |
| 3,842,270 | 10/1974 | Gregory et al. | 250/301 |
| 4,323,777 | 4/1982 | Baskins et al. | 250/339 |
| 4,351,642 | 9/1982 | Bonavent et al. | 23/230 |
| 4,501,324 | 2/1985 | Sandiford et al. | 166/250 |
| 4,536,322 | 8/1985 | Amstutz et al. | 252/301 |
| 4,555,627 | 11/1985 | McRae, Jr. | 250/334 |
| 4,632,807 | 12/1986 | Marsoner | 422/68 |
| 4,643,877 | 2/1987 | Opitz et al. | 422/68 |
| 4,644,354 | 2/1987 | Kidd | 340/870 |
| 4,661,320 | 4/1987 | Ito et al. | 422/86 |
| 4,662,940 | 5/1987 | Monier | 106/33 |
| 4,677,078 | 6/1987 | Minten et al. | 436/136 |
| 4,709,577 | 12/1987 | Thompson | 73/40 |
| 4,752,447 | 6/1988 | Kimmel et al. | 422/56 |
| 4,754,136 | 6/1988 | Blakely | 250/301 |
| 4,755,469 | 7/1988 | Showalter et al. | 436/27 |
| 4,758,366 | 7/1988 | Parekh | 252/68 |
| 4,762,420 | 8/1988 | Bowley | 356/436 |
| 4,770,028 | 9/1988 | Flippo, Jr. | 73/40 |
| 4,771,006 | 9/1988 | Miller et al. | 436/126 |
| 4,773,422 | 9/1988 | Isaacson et al. | 128/633 |
| 4,782,234 | 11/1988 | Caudyk et al. | 250/372 |
| 4,802,761 | 2/1989 | Bowen et al. | 356/300 |
| 4,863,694 | 9/1989 | Kimmel et al. | 422/86 |
| 4,892,383 | 1/1990 | Klainer et al. | 350/96 |
| 4,897,551 | 1/1990 | Gersh et al. | 250/461 |
| 4,899,047 | 2/1990 | Cary et al. | 250/227 |
| 4,912,051 | 3/1990 | Zaromb | 436/178 |
| 4,963,745 | 10/1990 | Maggard | 250/343 |

FOREIGN PATENT DOCUMENTS

| | | | |
|---|---|---|---|
| 285251 | 10/1988 | European Pat. Off. | 250/339 |
| 53-97491 | 8/1978 | Japan | 250/343 |
| 61-17037 | 1/1986 | Japan . | |
| 1313131 | 4/1973 | United Kingdom . | |
| 2142955 | 1/1985 | United Kingdom . | |

OTHER PUBLICATIONS

Louw et al., "A Simple Directly Combined Gas-Chromatographic-Infrared Spectroscopic System for Identification of Low Molecular Weight Hydrocarbons", Applied Spectroscopy, vol. 29, No. 1, 1975, pp. 15-24.

Telfair et al. "A Microcomputer-Controlled Infrared Analtter for Multi-Component Analysis", American Laboratory, vol. 8, No. 11, Nov. 1976, pp. 91-92, 94, 96; 98-100.

Kelly et al, "Prediction of Gasoline Octane Numbers from Near-Infrared Spectral Features in the Range 660-1215 nm", Anal. Chem. vol. 61, No. 4, Feb. 1989, pp. 313-320.

Primary Examiner—Constantine Hannaher
Assistant Examiner—Edward J. Glick
Attorney, Agent, or Firm—Thomas J. Engellenner; James E. Maslow

[57] ABSTRACT

Method and apparatus for monitoring hydrocarbon-based fuel properties by measuring the presence and amount of fuel component molecules in the fuel solution. Detection is made of absorption related to signature vibrational modes associated with the fuel component molecules when excited in the mid-IR. In one embodiment, a mid-IR light source illuminates the fuel in-situ and a narrow bandwidth detector associated with a vibrational mode signature detects absorbance as an indication of the presence and quantity of the fuel component in solution. From the determined fuel component quantity and known characteristics, the fuel solution properties are predicted. In one embodiment, octane rating and vapor pressure for a fuel solution is determined in-situ and in real time.

10 Claims, 6 Drawing Sheets

METHODS AND APPARATUS FOR DETERMINING HYDROCARBON FUEL PROPERTIES

BACKGROUND OF THE INVENTION

The field of the present invention is material analysis and, in particular, methods and apparatus for evaluation of the properties of hydrocarbon fuels.

It is of great interest to be able to ascertain with specificity, among other properties, the octane rating and vapor pressure of hydrocarbon-based fuels. These fuels, such as gasolines, are typically formulated as blends of various components, and it is therefore of interest to be able to identify and quantify such components. These data are useful both during production of such fuels at the refinery and during delivery of such fuels to the end-user. In either case, with these data, the producer, for production control purposes, or the consumer, to meet engine requirements or for comparative purposes, can assess the quality or value of the product at hand. However, while the producer normally employs elaborate testing procedures to obtain such data, the end-user consumer is typically limited to trusting the rating posted at the pump.

Octane numbers are conventionally determined and stated according to several known ASTM methods. For example, a research octane number (RON) can be determined according to ASTM Method 2699-84, and a motor octane number (MON) can be determined according to ASTM Method 2700-84. In addition, the conventional pump octane rating is determined as one-half of the sum of RON plus MON.

Present fuel components which affect the octane rating and vapor pressure of hydrocarbon fuels include MTBE (an ether-based fuel enhancer), aromatics (such as benzene, toluene and xylene), and alcohols (such as ethanol and methanol). MTBEs typically have an octane rating of about 110, aromatics typically have an octane rating of about 105, and alcohols typically have an octane rating of about 114.

Therefore, by determining the presence and volume percent of these components in a conventional hydrocarbon fuel solution, the overall octane rating (along with other physical parameters such as vapor pressure of the fuel solution) can be determined.

Various methods are known for the evaluation of fuel properties. Conventional spectroscopy techniques enable sampling and evaluation of a fuel's components, but the equipment is both expensive and ordinarily not available for real-time, in-situ evaluation of a delivered product.

One method of evaluating fuel properties is known as near-IR spectroscopy, in which a sample is excited with light from a near-IR light source. Since known fuel components exhibit characteristic vibrational mode overtones when excited in the near-IR, the vibrations of unknown constituents can be evaluated and classified accordingly. The typical evaluative process is complex, involving substantial non-linear data comparisons. Kelly, et al, describe such a method in "Prediction of Gasoline Octane Numbers from Near-Infrared Spectral Features in the Range 660-1215 nm," Vol. 61, *Analytical Chemistry*, No. 4, p.313, Feb. 15, 1989, in which vibrational overtones and combination bands of CH groups of methyl, methylene, aromatic, and olefinic functions were observed in the near-IR spectral region of 660-1215 nm (15,150-8,200 wavenumbers). With the aid of multivariate statistical analysis, the spectral features were correlated to various fuel quality parameters, including octane number.

Maggard, U.S. Pat. No. 4,963,745 is an example of near infrared absorbance evaluation between 1200 and 1236 nm applied to the methyne band along with the tertiary butyl band, indicative of sources of free radicals which seem to lead to smooth combustion. The signal processing techniques used, however, are complex, including first, second, third, and fourth or higher derivative processing; division of absorbance at one wavelength by those at other wavelengths for noise reduction, spectral subtraction for absorbance differentiation; and combinations thereof, as well as various known curve fitting techniques, such as disclosed in Maggard, U.S. Pat. No. 4,963,745, which are incorporated herein by reference.

It is therefore an object of the present invention to provide a simplified method and apparatus for fuel property detection.

It is another object of the present invention to provide a relatively inexpensive, real-time, in-situ detection method and apparatus for detection of the properties of a hydrocarbon solution.

It is still another object of the present invention to provide a simplified method and apparatus for obtaining absorption data linearly relating to the quantity of components in a fuel solution and from which predicting fuel properties without complex mathematical processing techniques.

SUMMARY OF THE INVENTION

The present invention is based on a recognition that the molecules of components of a hydrocarbon solution each exhibit characteristic primary, overtone and/or combination vibrational modes (also referred to herein as "signature" or "signature modes") when excited in the mid-IR range, about 4000-500 wavenumbers (about 2,500 to 20,000 nm), that such signatures are exhibited in terms of absorbance of the excitation energy, and that such absorbance can be detected and expressed as detection data which can be correlated linearly with volume percent of the associated component in solution. Where the properties of the components are known, such as octane, vapor pressure, and the like, the volume percent quantification of these components can be used in practice of the invention to characterize the total volume of hydrocarbon solution. Therefore, in one aspect of the invention, molecules of fuel components in a hydrocarbon fuel solution are excited with mid-IR light, and the amount of absorption exhibited by these excited molecules is detected and used to identify the presence of and to quantify the volume percent of the fuel components in solution. From this data, and knowledge of the known properties of the fuel components, the properties of the fuel solution are determined in-situ and in real time.

Accordingly, in one embodiment of the invention, a transparent examination vessel is disposed within a fuel-flow path, and the fuel or a portion thereof, flows through the vessel in the regular course of fuel transfer. A broadband mid-IR light source is placed on one side of the vessel and a detector associated with a particular fuel component of interest is located on the other side of the vessel in line with the light source. A narrow-band filter is interposed between the light source and the detector; the filter narrows the mid-IR light emissions to a narrow band associated with a signature mode determined to be characteristic of the fuel component of interest. Thus, the flowing fuel is illuminated in the mid-IR from one side of the vessel, the narrow band of interest is isolated by the assigned narrow-band filter, and the filter output is read by the detector on the opposite side of the vessel indicative of the amount of light absorption stemming from such signature mode.

The absorption data from the detector is processed in a processing section of the device, in which the data is linearly correlated to volume percent of the fuel component in solution. In a preferred embodiment, the absorption data is linearly correlated to octane rating and vapor pressure of the fuel solution, as correlated to stored values in a look-up table of the processing section, and a display output is then generated accordingly. Likewise, other components may be found and quantified in a similar manner. Where a plurality of components are of interest, a plurality of filters and associated detectors are employed, respectively, and the plurality of detection data is processed and then combined in an additive process to obtain total octane rating and vapor pressure for the fuel.

Because of such linearity and simplicity, the invention enables fuel properties to be easily determined and displayed. Such fuel properties may include a pump octane rating equivalent to the ASTM PON rating, vapor pressure, and various other properties of the components of interest. In fact, while the ASTM methods of obtaining RON and MON are labor-intensive laboratory procedures, the present invention provides an equivalent pump octane rating in-situ and in realtime. The present invention is therefore a valuable addition to the art of fuels properties detection.

BRIEF DESCRIPTION OF THE DRAWINGS

These and other features and advantages of the present invention will be more fully understood by reference to the following detailed description in conjunction with the attached drawing in which like reference numerals refer to like elements and in which.

DETAILED DESCRIPTION

Figure 1:
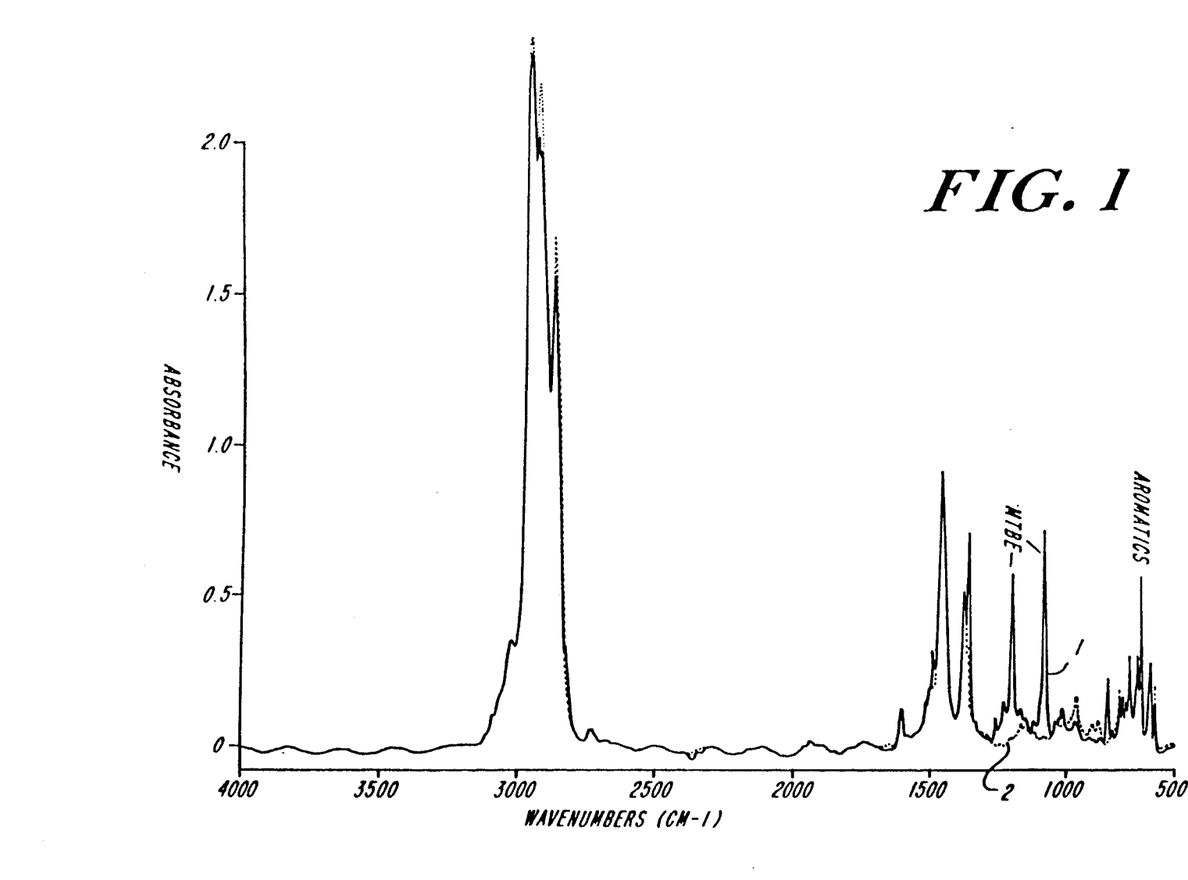
FIG. 1 is a graphical comparison of absorbance (in arbitrary units) exhibited by fuel enhancers in two gasolines, one at 94 octane (solid line trace "1") having MTBE and aromatic octane enhancers, and one at 86 octane (dotted line trace "2") without MTBE, both illuminated in the mid-IR range of about 4000 to 500 wavenumbers (cm$^{-1}$), in practice of the invention.

FIG. 1 is a graphical comparison of absorbance exhibited by the components of two gasolines, one gasoline at 94 octane and having MTBE and aromatic octane enhancers (curve 1), and one at 86 octane without MTBE (curve 2), both illuminated in the mid-IR light range of about 4000 to 500 wavenumbers (cm$^{-1}$). MTBE is a complex molecule and therefore has a plurality of signatures, such as at 1100 and 1200 wavenumbers. In practice of the present invention, we have selected a particular signature for MTBE. This mode appears as an absorption peak at about 1200 wavenumbers on curve 1. This peak stands out over the relatively flat curve 2 for the fuel without MTBE at 1200 wavenumbers. Therefore, a detector limited to a narrow spectrum at about 1200 wavenumbers can detect a change in light intensity attributed to absorption caused by the molecular vibrations associated with MTBE excited at about 1200 wavenumbers.

Figure 2:
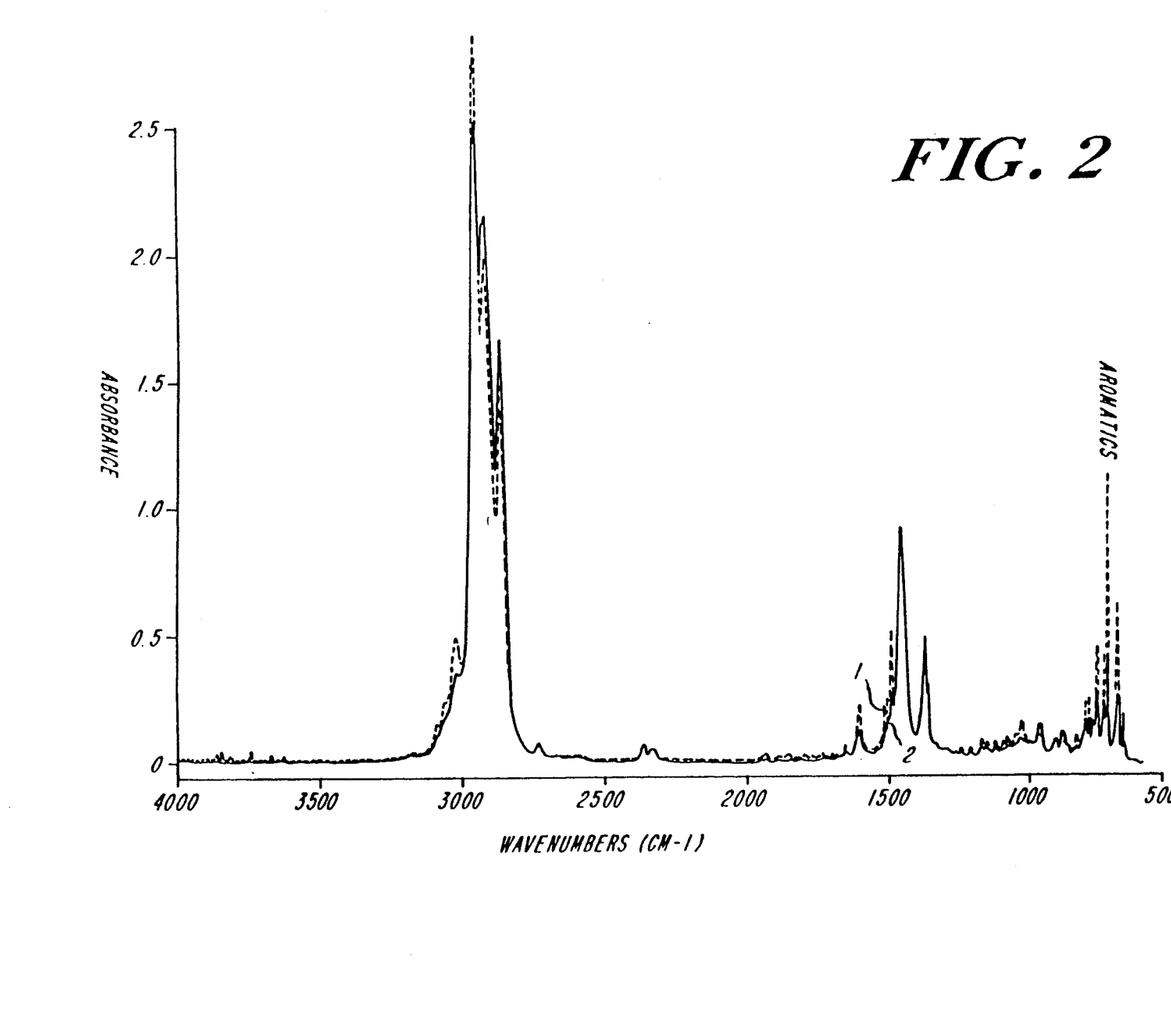
FIG. 2 is a graphical comparison of absorbance (in arbitrary units) exhibited by fuel enhancers in two gasolines, one at 92.8 octane (dotted line trace "1") having aromatic octane enhancers, and one at 87.1 octane (solid line trace "2") without aromatics, both illuminated in the mid-IR range of about 4000 to 500 wavenumbers (cm$^{-1}$), in practice of the invention.

FIG. 2 is a similar comparison of absorbance exhibited by the components of two gasolines, one gasoline at 92.8 octane (curve 1) and one at 87.1 octane (curve 2), with different levels of aromatic fuel components added for octane enhancement. A particular aromatic formulation itself also may be complex, and yet, as shown, a vibrational mode signature of aromatics is found at about 700 wavenumbers, and therefore a detector limited to a narrow spectrum at about 700 wavenumbers can detect variations in light intensity attributed to absorption caused by the vibrations associated with aromatics.

Figure 3:
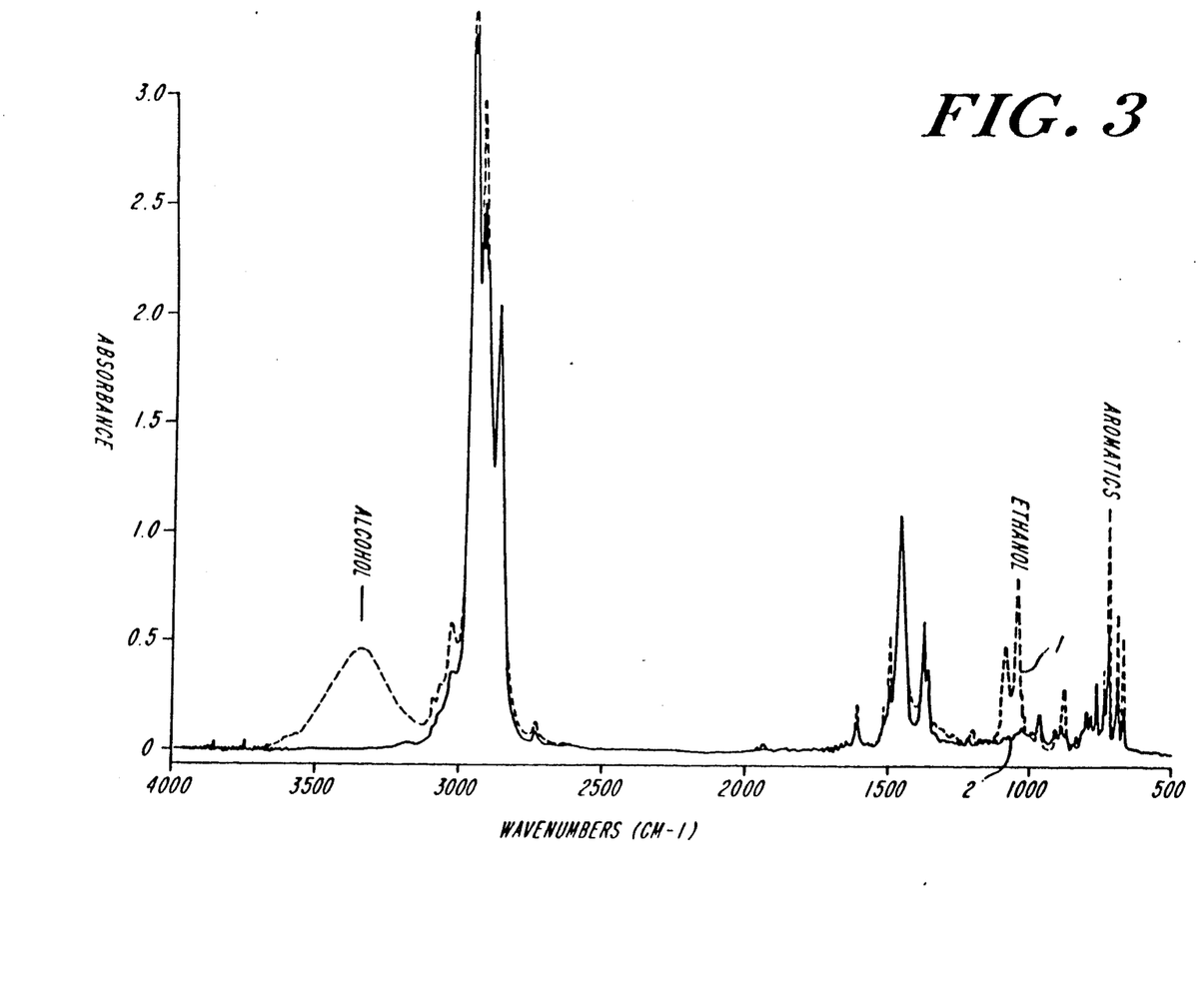
FIG. 3 is a graphical comparison of absorbance (in arbitrary units) exhibited by fuel enhancers in two gasolines, one at 91.2 octane (dotted line trace "1") having alcohol and aromatic octane enhancers, and one at 87.3 octane (solid line trace "2") without alcohol, both illuminated in the mid-IR range of about 4000 to 500 wavenumbers cm$^{-1}$), in practice of the invention.

FIG. 3 is a similar comparison of absorbance exhibited by the components of two gasolines, one at 91.2 octane (curve 1) and one at 87.3 octane (curve 2). The 91.2 octane fuel uses alcohol (including ethanol) and aromatics as octane enhancers. The 87.3 octane fuel lacks the alcohol fuel enhancers. As shown, a vibrational mode signature for alcohols is at about 3300 wavenumbers, and therefore a detector limited to a narrow spectrum at about 3300 wavenumbers can detect variations in light intensity attributed to absorption caused by the vibrations associated with mid-IR excited alcohols. As well, ethanol has a unique signature at 1100 wavenumbers, and a detector limited to about 1100 wavenumbers can be employed to detect the percent of ethanol excited at 1100 wavenumbers, if desired.

Figure 4:
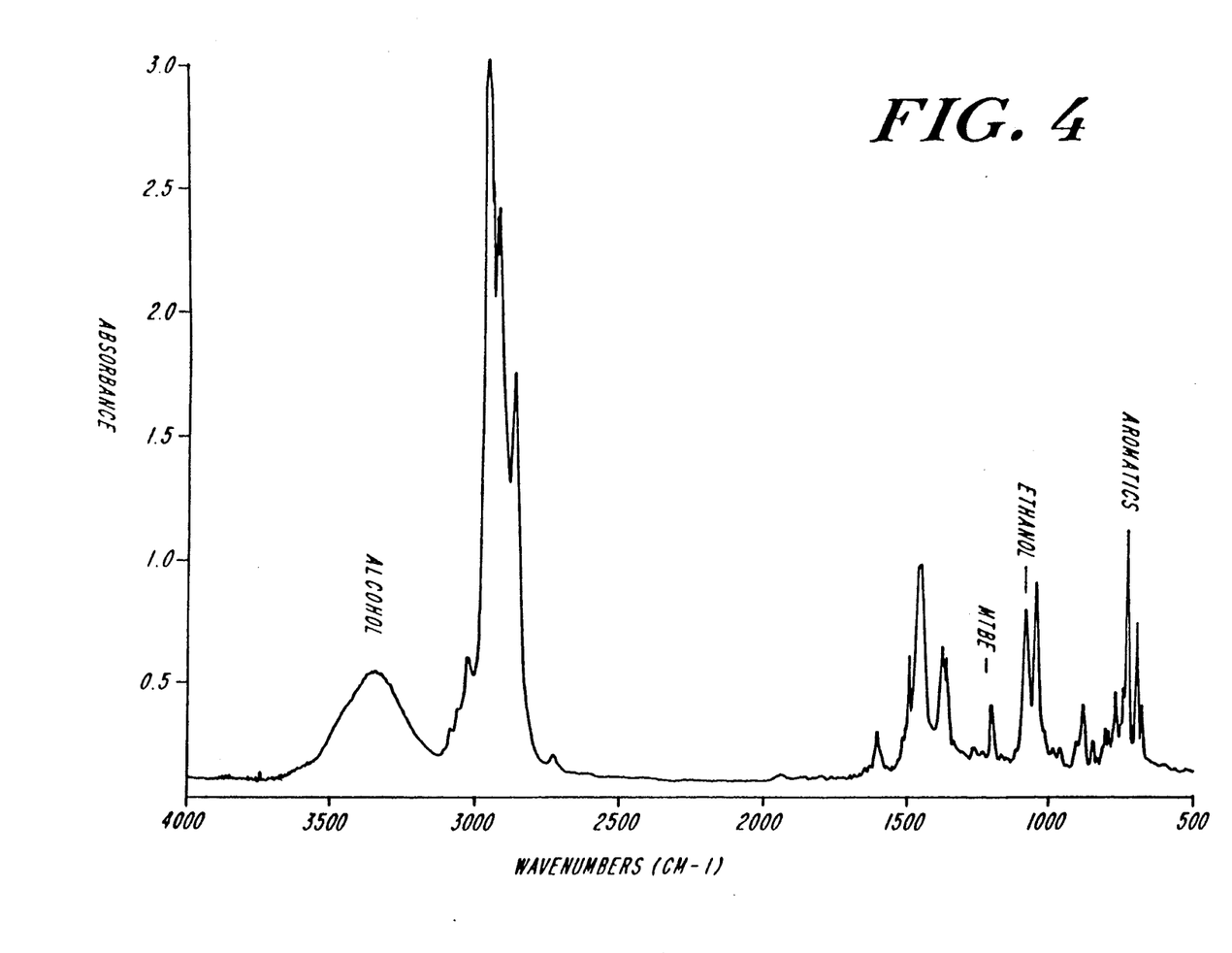
FIG. 4 is a graphical representation of absorbance (in arbitrary units) exhibited by MTBE, aromatic, alcohol octane enhancers in a gasoline blend, evaluated in practice of the invention.

FIG. 4 is a graphical representation of absorbance exhibited by a gasoline formulated with a blend of MTBE, aromatic, alcohol (including ethanol) octane enhancers, detected according to the invention. The peak at 1200 wavenumbers indicates MTBE quantity, the peaks at 500-800 wavenumbers indicate aromatic quantity, the peak at 3300 wavenumbers indicates alcohol quantity, and the peak at 1100 wavenumbers indicates ethanol. In practice of the invention, the fuel in FIG. 4 was accurately predicted to have an octane rating of 93.6.

Figure 5:
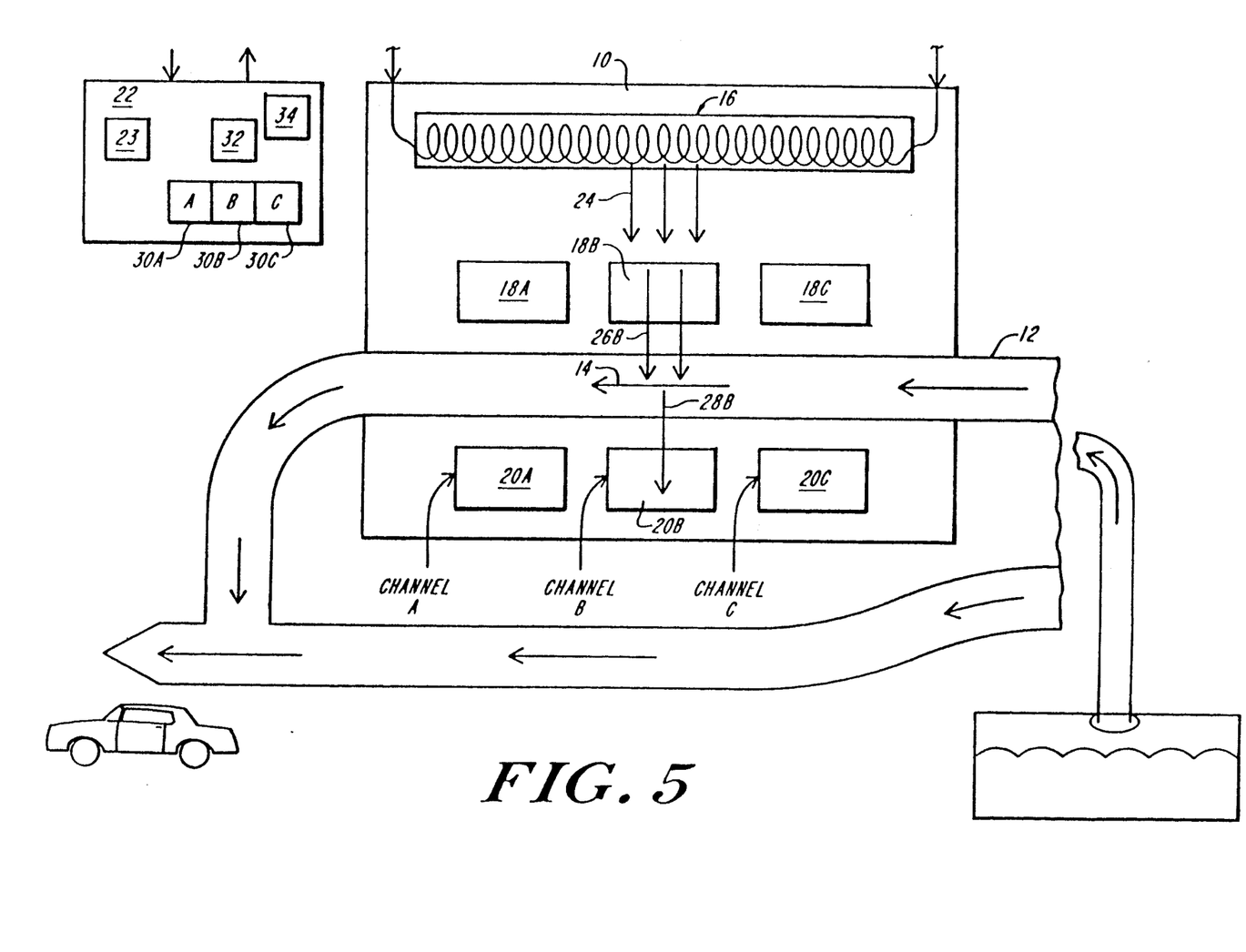
FIG. 5 is a schematic representation of a multi-channel fuel properties monitor according to an embodiment of the invention for detection and quantification of fuel enhancers, with MTBE assigned to channel A, aromatics assigned to channel B, and alcohols assigned to channel C.

FIG. 5 is a schematic representation of a multi-channel fuel properties monitor 10 for detection and evaluation of components of the fuel flowing through examination vessel or tube 12, according to an embodiment of the invention. In this embodiment, MTBE is assigned to channel A, aromatics is assigned to channel B, and alcohols is assigned to channel C. (Other channels may be included for ethanol, methanol, etc.)

Monitor 10 enables evaluation of fuel in-situ. In large-capacity operations, a shunt line is tied into the primary fuel line so as to deliver a measurable stream to monitor 10 representative of the larger supply of flowing fuel. This avoids impeding fuel flow in the primary fuel line.

Therefore, in the embodiment of FIG. 5, a portion 14 see arrow 14) of the pumped fuel otherwise being pumped from the fuel source (e.g., a fuel storage tank) to the destination (e.g., an automobile fuel tank) is shunted through tube 12. Advantageously, this arrangement avoids the extra steps of withdrawing a separate sample from the tank and evaluating the sample removed from the fuel flow, and eliminates the waste and inconvenience associated therewith.

Mid-IR light source 16 (e.g., a heated element acting as a black body radiator) is provided on one side of tube 12 for illuminating the flowing fuel 14. A respective detector 20A, 20B, 20C assigned to channels A,B,C, respectively, is provided on the other side of the tube for detecting absorption associated with the presence of the assigned fuel component. Because each detector is assigned to a specific fuel component of interest, each detector's input is limited to that narrow portion of the mid-IR spectrum as associated with a selected vibrational mode signature which has been determined to be characteristic of the assigned fuel component.

Isolation of each detector to an assigned fuel component is achieved in this embodiment by interposing a filter 18A, 18B, 18C between light source 16 and detectors 20A, 20B, 20C, respectively. Each filter passes a narrow band of mid-IR light associated with the signature vibrational mode of the assigned fuel component. Additional filters and detectors may be employed for detection of yet other components, such as ethanol and methanol. (Each filter may take the form of a window on a detector device itself, rather than as a separate discrete component, or may even be eliminated where the detection is otherwise limited to a narrow band of interest.)

The signal leads for lamp 16 and detectors 20A, 20B, 20C are connected to a processor and control unit 22 for driving of the lamp, for processing of detection signal outputs from the detectors, and for display of readout information at displays 30A (MBTE volume percent), 30B (aromatics volume percent), and 30C (alcohols volume percent). Displays 32 and 34 are also provide for indication of predicted equivalent octane rating for the fuel solution.

In operation, as fuel is pumped through tube 12, the mid-IR light energy 24 from source 16 passes through filters 18A, 18B, 18C, and therefore is limited to respective assigned spectra of interest. As shown with respect to channel B, for example, the presence and amount of aromatics in the fuel is determined when mid-IR light output 26B from filter 18B passes through fuel 14 and detector 20B then detects the attentuated beam 28B representative of the presence and amount of aromatics. The detector output varies according to absorbance level, and this intensity is then processed in processor and control unit 22 and an indication of the presence of aromatics (based upon detected light absorption) and the amount as volume percent in solution (according to amount of absorption), which is indicated at display 30B. (Channels A and C operate analogously.)

Figure 6:
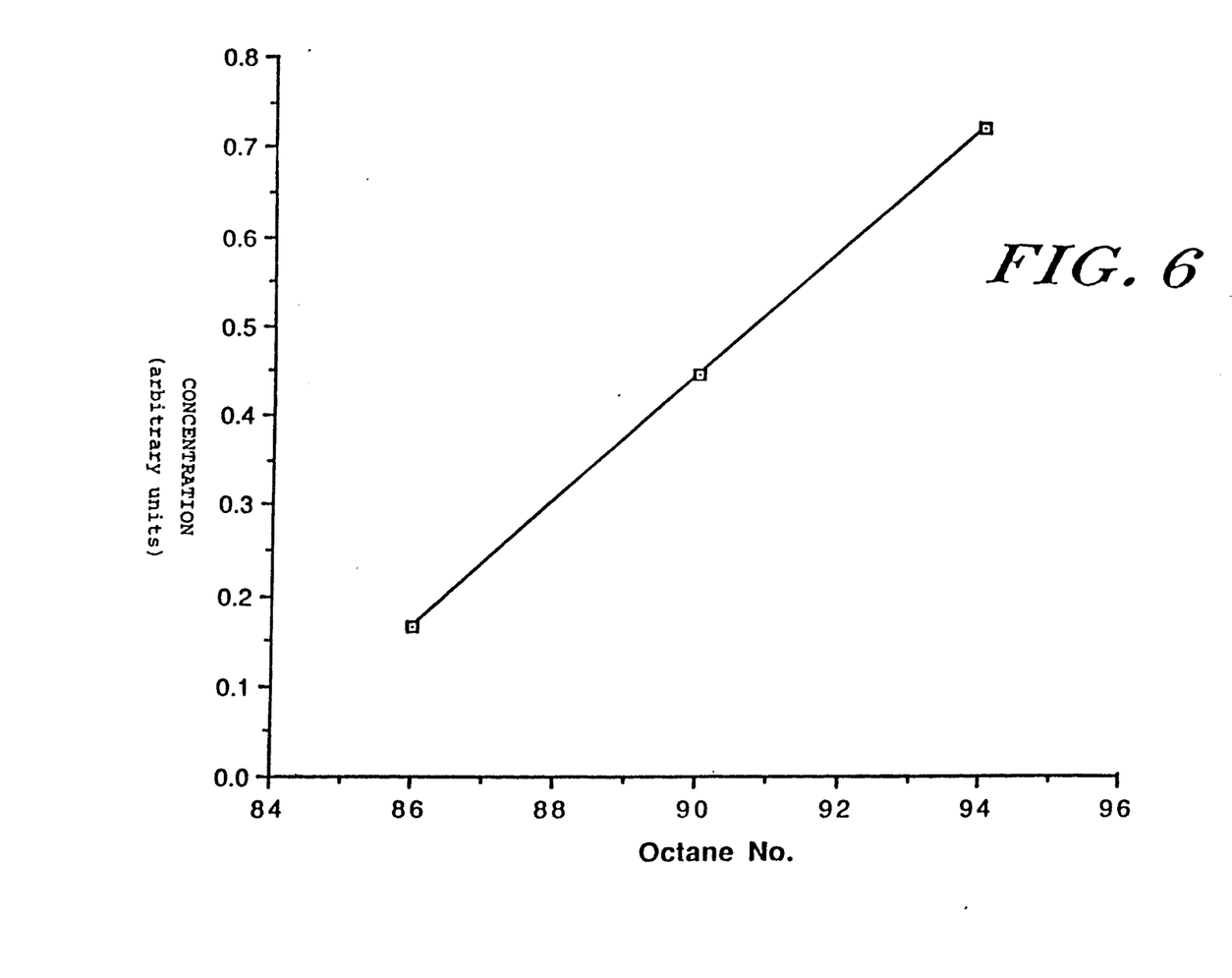
FIG. 6 is a graphical representation of concentration (in arbitrary units) of fuel enhancer and octane rating for a sample fuel having a single enhancer, in practice of the invention.

According to Beer's Law, absorbance is directly related to concentration of a fuel enhancer in a fuel solution. Thus a given detector output is used as a direct indication of concentration of the detected fuel enhancer in the fuel under test. FIG. 6 shows a linear relationship between concentration of a single enhancer and octane rating in practice of the invention. However, for fuels having a combination of enhancers, the outputs of the several detectors must be appropriately weighted and added to obtain octane number. This weighting and adding may be executed in a conventional manner.

Therefore, for a fuel having a plurality of octane enhancers, and with the presence and amount of MTBE, aromatics, and alcohols now being obtained by the invention, and with their individual octane ratings being well known and stored in a look-up table 23, the processor and control unit 22 combines these individual octane ratings, properly weighted according to the determined volume percent in solution for each of such components, and displays the predicted total fuel octane rating at rating display 32. In a like manner, the fuel's predicted total vapor pressure can be determined and displayed at pressure display 34.

Notwithstanding the foregoing, under present EPA regulations, alcohol content is specified at the pump, and therefore a simplified embodiment of the invention is programmed with the known alcohol content of the fuel supply under test, and the present detection function is then limited to other fuel components, such as to MTBE and aromatics. Thereafter, total fuel properties are computed as otherwise set forth herein.

Furthermore, while vibrational modes have been expressed above as measured according to peaks in the absorbance curve, the present invention is operable whether the data is peak, rms, or area under the curve, as long as it expresses the significance of the narrow detection band associated with the component of interest.

In sum, the present invention benefits from the recognition that fuel component molecules in a hydrocarbon fuel solution, when excited in the mid-IR, absorb light at their vibrational modes. Each such fuel component has known properties and is associated with at least one of its vibrational modes as a signature. By detecting the amount of absorption at a selected narrow bandwidth associated with that vibrational mode signature, it is possible to qualify and quantify properties of the fuel solution. Therefore, in practice of the invention, a fuel supply is subjected to mid-IR excitation, and for each fuel component of interest a detector limited to an assigned narrow detection band indicates the presence (by detecting absorbance) and the amount (by quantifying the amount of absorbance) of the assigned fuel component according to its vibrational mode signature within that narrow detection band. The fuel solution is then characterized from such data.

It will be understood that the above description pertains to only several embodiments of the present invention. That is, the description is provided by way of illustration and not by way of limitation. For example, while particular vibrational modes within the mid-IR spectrum have been selected and used as preferred signatures for the above classes of fuel components, other vibrational modes and other classes of fuel components can be selected consistent with the present invention. Thus, the classes of fuel components identified above, but reformulated, or newly formulated fuel components other than those identified above, having the above or other vibrational modes, are also within the spirit and scope of the present invention. Furthermore, in another embodiment of the invention, more than one signature is used to characterize a particular fuel component which is otherwise difficult to identify by observation of only one of its vibrational modes, and a respective detector is then assigned to each respective mode. The invention is further characterized according to the following claims.

What is claimed is:

1. Apparatus for determining the properties of a hydrocarbon-based fuel based on analysis of the components of the fuel, the apparatus comprising:
   an examination vessel for receiving a hydrocarbon-based fuel sample;
   a mid-IR light source which illuminates the fuel sample;
   detection means for detecting a plurality of fuel components, each fuel component having known characteristics including at least one known absorbance value associated with a known quantity of that fuel component, the detection means comprising, for each one of the plurality of fuel components, at least one light absorption detector assigned to a narrow spectral band centered about a wavelength associated with a signature vibrational mode of the respective fuel component and selected from the group consisting of:
   700 wavenumbers, for the measurement of aromatic-based fuel components,
   1100 wavenumbers, for the measurement of ethanol fuel components,
   1200 wavenumbers, for the measurement of MTBE fuel components, and
   3300 wavenumbers, for the measurement of alcohol-based fuel components;
   each detector output expressing a detected absorbance value indicative of the quantity of the detected fuel component; and
   correlation means for predicting the properties of the fuel based upon correlation of the known characteristics of the fuel components with the output of the detectors.

2. The apparatus of claim 1 wherein the correlation means performs a correlation between the amount of the detected absorbance value with the volume percent in solution of the fuel component.

3. The apparatus of claim 2 wherein the correlation means further performs a correlation between the amount of the detected absorbance value to octane rating and vapor pressure of the fuel.

4. The apparatus of claim 1 wherein the examination vessel is a shunt tube for sampling a flowing portion of the fuel for in-situ determination of the fuel properties.

5. The apparatus of claim 1 wherein the mid-IR light source comprises a heated element acting as a block body radiator, having a bandwidth of 4000-500 wavenumbers.

6. The apparatus of claim 1 wherein the correlation means comprises a microprocessor.

7. The apparatus of claim 1 wherein each respective light absorption detector comprises a narrow band filter for limiting the bandwidth of the detector to a narrow range in the mid-IR spectrum centered about the frequency of the signature vibrational mode of the respective one of the plurality of components.

8. Method for determining the properties of a hydrocarbon-based fuel based on analysis of the components of the fuel, comprising the steps of:
   illuminating a stream of hydrocarbon-based fuel with mid-IR light;
   obtaining an absorbance value associated with a quantity of fuel component for each of a plurality of fuel components by evaluating the illuminated stream with a respective light absorption detector assigned to a narrow spectral band centered about a wavelength associated with a signature vibrational mode of the respective fuel component and selected from the group consisting of:
   700 wavenumbers, for the measurement of aromatic-based fuel components,
   1100 wavenumbers, for the measurement of ethanol fuel components,
   1200 wavenumbers, for the measurement of MTBE fuel components, and
   3300 wavenumbers, for the measurement of alcohol-based fuel components;
   each detector output expressing a detected absorbance value indicative of the quantity of the detected fuel component; and
   predicting the properties of the fuel based upon correlation of the known characteristics of the fuel components with the detected absorbance values outputted by the detectors.

9. The method of claim 8 wherein the predicting further comprises correlating the detected absorbance value with the volume percent in solution of the fuel component.

10. The method of claim 9 wherein the predicting further comprises correlating the absorbance value to octane rating and vapor pressure of the fuel.

* * * * *